United States Patent [19]

Ushijima et al.

[11] Patent Number: 4,987,235
[45] Date of Patent: Jan. 22, 1991

[54] ISOINDOLINE DERIVATIVES AND PROCESSES FOR THEIR PREPARATION

[75] Inventors: Ryosuke Ushijima; Susumu Nakagawa, both of Okazaki; Eiichi Mano, Kariya, all of Japan

[73] Assignee: Banyu Pharmaceutical Co., Ltd., Tokyo, Japan

[21] Appl. No.: 267,094

[22] Filed: Nov. 3, 1988

Related U.S. Application Data

[62] Division of Ser. No. 225,645, Jul. 28, 1988, abandoned.

[30] Foreign Application Priority Data

Dec. 9, 1985 [JP] Japan .................................. 60-275196
Dec. 9, 1985 [JP] Japan .................................. 60-275197
Dec. 18, 1985 [JP] Japan .................................. 60-283080

[51] Int. Cl.$^5$ ............... C07D 491/056; C07D 209/044
[52] U.S. Cl. ...................................... 548/430; 548/482
[58] Field of Search ................................ 548/482, 430

[56] References Cited

U.S. PATENT DOCUMENTS 4,168,309 9/1979 Ayres ..................................... 540/222
4,677,100 6/1987 Nakagawa et al. ................. 514/202

OTHER PUBLICATIONS

Nakagawa et al., ICAAC Abstract, Sep. 1985.

Primary Examiner—Mary E. Ceperley
Attorney, Agent, or Firm—Oblon, Spivak, McClelland, Maier & Neustadt

[57] ABSTRACT

A compound having the formula:

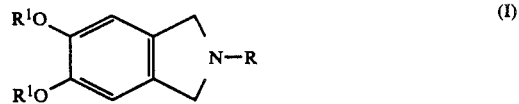

(I)

wherein R is a hydrogen atom, a lower alkyl group, an alkanoyl group, an aralkyl group, an alkylsulfonyl group or an arylsulfonyl group, and $R^1$ is a hydrogen atom or a protecting group for a hydroxyl group, or a salt thereof.

1 Claim, No Drawings

ISOINDOLINE DERIVATIVES AND PROCESSES FOR THEIR PREPARATION

This is a division of application Ser. No. 225,645, filed July 28, 1988, now abandoned.

The present invention relates to novel isoindoline derivatives and processes for their preparation.

"Organic Syntheses", Coll. Vol., 5, 406, ibid., 5, 1064 discloses a general process represented by the following scheme for the synthesis of isoindoline having no substituent on the benzene nucleus.

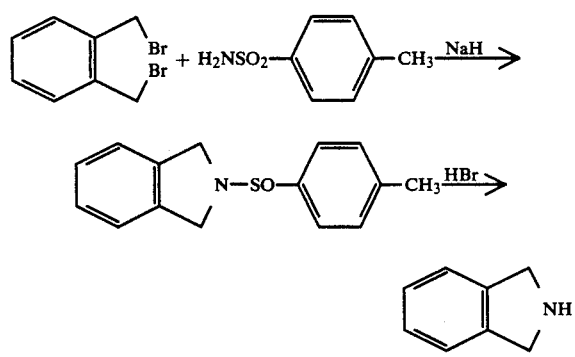

Heretofore, it has believed difficult to introduce hydroxyl groups directly to the 5- and 6-positions of isoindoline, and such introduction is expected to involve a number of process steps, such being undesirable from the industrial point of view.

The compounds of the present invention having substituents at the 5- and 6-positions or at the 2-, 5-, and 6-positions of an isoindoline nucleus, are novel compounds not disclosed in literatures.

The present inventors have conducted extensive researches with an aim to develop novel isoindoline derivatives, and as a result, have found it possible to produce novel compounds of the formula I by either process A or process B as identified hereinafter.

Namely, the present invention provides a compound having the formula:

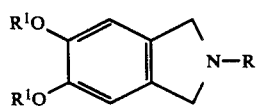

(I)

wherein R is a hydrogen atom, a lower alkyl group, an alkanoyl group, an aralkyl group, an alkylsulfonyl group or an arylsulfonyl group, and $R^1$ is a hydrogen atom or a protecting group for a hydroxyl group, or a salt thereof.

The compound of the formula I can be produced in good yield by either process A or process B as follows.

PROCESS A

This process comprises reacting a secondary amine having the formula:

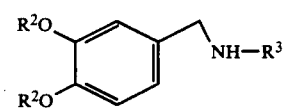

(IV)

wherein $R^2$ is a protecting group for a hydroxyl group, and $R^3$ is a lower alkyl group, an aralkyl group, an alkylsulfonyl group or an arylsulfonyl group, with formaldehyde or a reagent capable of forming formaldehyde under the reaction condition and a hydrogen halide, to form a compound having the formula:

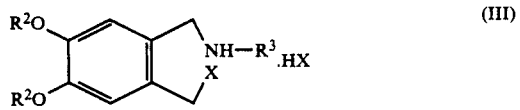

(III)

wherein X is a halogen atom, and $R^2$ and $R^3$ are as defined above; followed by dehydrohalogenation to obtain a compound having the formula:

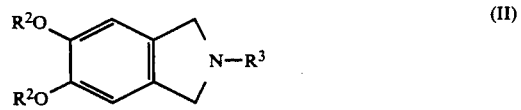

(II)

ps wherein $R^2$ and $R^3$ are as defined above, or a salt thereof; and if necessary, removing the protecting group, or removing the protecting group, followed by at least one step selected from the group consisting of (a) acylation, (b) N-alkylation and (c) N-aralkylation.

PROCESS B

This process comprises reacting a compound having the formula:

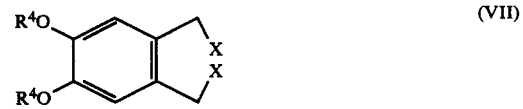

(VII)

wherein $R^4$ is a protecting group for a hydroxyl group, and X is a halogen atom, with a compound having the formula:

$R^5$—$NH_2$ (VI)

wherein $R^5$ is a hydrogen atom, a lower alkyl group, an aralkyl group, an alkylsulfonyl group or an arylsulfonyl group, to form a compound having the formula:

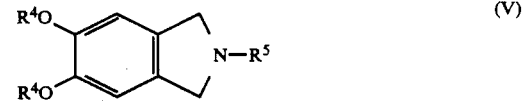

(V)

wherein $R^4$ and $R^5$ are as defined above, or a salt thereof; and if necessary, removing the protecting group, or removing the protecting group, followed by at least one step selected from the group consisting of (a) acylation, (b) N-alkylation and (c) N-aralkylation.

Now, the present invention will be described in detail with reference to the preferred embodiments.

Firstly, the terms used in this specification will be defined.

The lower alkyl group means a straight chain or branched alkyl group having from 1 to 4 carbon atoms, such as methyl, ethyl, propyl, isopropyl, n-butyl or t-butyl. Particularly preferred are methyl, ethyl and propyl.

The alkanoyl group means an alkanoyl group having from 2 to 6 carbon atoms, such as acetyl, propionyl or butyryl. Particularly preferred are acetyl and propionyl.

The aralkyl group means an aralkyl group having from 7 to 12 carbon atoms, such as benzyl, p-methoxybenzyl, phenetyl or (1-naphthyl)methyl. Particularly preferred are benzyl and p-methoxybenzyl.

The alkylsulfonyl group means an alkylsulfonyl group such as methanesulfonyl or ethanesulfonyl. Particularly preferred is methanesulfonyl.

The arylsulfonyl group means an arylsulfonyl group such as benzenesulfonyl or p-toluenesulfonyl. Particularly preferred is p-toluenesulfonyl.

The halogen atom means a halogen atom such as chlorine or bromine. Particularly preferred is chlorine.

The protecting group for a hydroxyl group includes methyl, benzyl, ethoxycarbonyl and carbonate which can readily be removed by e.g. acidic hydrolysis or catalytic reduction. Further, the protecting group includes a case where the adjacent hydroxyl groups together form a cyclic acetal such as methylene acetal or ethylene acetal, or a cyclic ketal such as isopropylidene ketal.

Among the compounds of the formula I of the present invention, preferred are as follows:
1. 5,6-dihydroxyisoindoline
2. 5,6-dimethoxyisoindoline
3. 5,6-diacetoxyisoindoline
4. 5,6-dihydroxy-2-methylisoindoline
5. 5,6-dimethoxy-2-methylisoindoline
6. 5,6-diacetoxy-2-methylisoindoline
7. 2-benzyl-5,6-dihydroxyisoindoline
8. 2-benzyl-5,6-dimethoxyisoindoline
9. 5,6-diacetoxy-2-benzylisoindoline
10. 5,6-dimethoxy-2-p-tolylsulfonylisoindoline
11. 5,6-diacetoxy-2-p-tolylsulfonylisoindoline Now, the processes for the preparation of the compounds of the invention will be described. The compounds of the formula I may be prepared by either process A or process B as described below.

PROCESS A

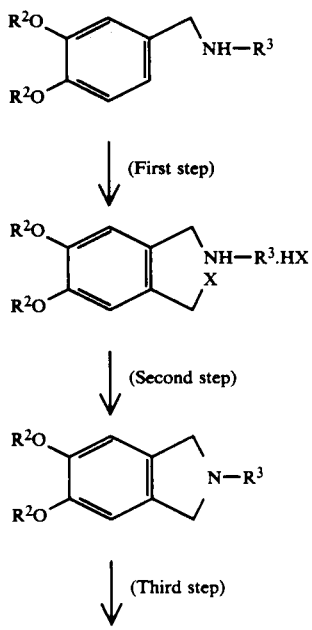

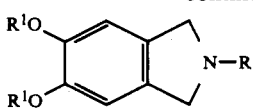

First Step

This step comprises reacting a secondary amine of the formula IV with formaldehyde or a reagent capable of forming formaldehyde under the reaction condition, in the presence of concentrated hydrochloric acid or hydrobromic acid, to form an N-(3,4-di-substituted-6-halomethylbenzyl)-N-substituted secondary amine of the formula III.

The formaldehyde or the reagent capable of forming formaldehyde under the reaction condition, includes formalin, paraformaldehyde, trioxane, methylene diacetate, methylene sulfate, chloromethyl acetate, bis-(acetoxymethyl) ether and methylal.

The reaction is conducted at a temperature of from 20° to 80° C. for a few hours in the presence of concentrated hydrochloric acid or hydrobromic acid in such a proportion that formaldehyde is used in an amount of from 1 to 4 mols to 1 mol of the secondary amine of the formula IV.

The resulting N-(3,4-di-substituted-6-halomethylbenzyl)-N-substituted secondary amine of the formula III can be purified in the form of its hydrochloride or hydrobromide by evaporating the reaction solvent to dryness under reduced pressure and washing the crystalline residue with acetone or recrystallizing the crystalline residue.

Second Step

This step comprises treating the N-(3,4-di-substituted-6-halomethylbenzyl)-N-substituted secondary amine of the formula III in the presence of an acid binding agent for dehydrohalogenation to obtain a compound of the formula II or its salt.

The reaction is conducted in an inert organic solvent such as benzene, toluene, xylene, methylene chloride or chloroform, or in a two-phase system of such an inert organic solvent and water, in the presence of an acid binding agent at a temperature of from 0° to 40° C. for from 0.5 to 15 hours. When the reaction is conducted in the two-phase system, a phase transfer catalyst as disclosed in "Phase Transfer Catalysis in Organic Synthesis" 1977, co-authored by W.P. Weber and G.W. Gokel; co-translated by Tabuchi and Nishida, may be employed. As such a phase transfer catalyst, there may be mentioned, for example, tetramethylammonium chloride, benzyltrimethylammonium chloride, benzyltriethylammonium chloride, benzyltributylammonium chloride, tetrabutylammonium bromide, tetrabutylammonium hydrogensulfate and trioctylmethylammonium chloride.

As the acid binding agent used for the reaction, there may be mentioned, for example, sodium hydroxide, potassium hydroxide, sodium carbonate and potassium carbonate.

Third Step

This step is an optional step to lead the compound of the formula II obtained in the second step to a compound of the formula I, as the case requires. Namely, the step comprises the removal of the protecting group or the removal of the protecting group, followed by at least one step selected from the group consisting of (a)

acylation, (b) N-alkylation and (c) N-aralkylation, to obtain the compound of the present invention.

Firstly, a method for the removal of the protecting group will be described.

Removal of the protecting group

The removal of the protecting group may be conducted in accordance with the methods disclosed in e.g. "Protective Groups in Organic Sysnthesis" authored by T.W. Greene, published in 1981 by Wiley Company, and "Protective Groups in Organic Chemistry" authored by J.F.W. McOmie, published in 1973 by Plenum Press. For example, acidic hydrolysis and catalytic reduction may be mentioned as preferred methods.

Acidic hydrolysis

The protecting group of the compound of the formula II can be removed by heating the compound with an acid in an amount of from 1 to 20 times, preferably from 3 to 10 times, relative to the compound of the formula II. As the acid, an inorganic acid such as hydrochloric acid, hydrobromic acid, hydroiodic acid or sulfuric acid, may be employed.

The hydrolysis may be facilitated by an addition of a suitable amount of acetic acid, propionic acid or phenol to the reaction solution. The reaction temperature may be from 70° to 130° C. The reaction can be completed within from 2 to 30 hours under reflux.

Catalytic reduction

The compound of the formula II is dissolved in water, methanol, ethanol, propanol, isopropanol, acetic acid, hydrochloric acid, hydrobromic acid, sulfuric acid or a mixed solution thereof, and catalytically reduced with 5–10% palladium carbon in an amount of from 5–20% by weight, preferably from 5 to 10% by weight, of the compound of the formula II, at a reaction temperature of from 20° to 80° C. for a reaction time of from 2 to 10 hours, to remove the protecting group.

When $R^3$ in the compound of the formula II is an aralkyl group such as benzyl, an alkylsulfonyl group such as methanesulfonyl or an arylsulfonyl group such as p-toluenesulfonyl, such an aralkyl or sulfonyl group can be a protecting group for an amino group. When such an aralkyl or sulfonyl group is removed, the treatment can be conducted in the same manner as in the case of the removal of the protecting group for a hydroxyl group. Further, by properly selecting the type of the protecting group and the reaction condition for the removal of the protecting group, it is also possible to remove only the protecting group for the amino group.

Now, the above-mentioned steps (a) to (d) will be described.

(a) Acylation

This acylation reaction can be conducted in a solvent not adversely affecting the reaction, such as acetic acid or trifluoroacetic acid by reacting the compound of the formula II or its salt with an excess amount of a carboxylic anhydride at a reaction temperature of from 10° to 80° C. for from 0.5 to 48 hours, if necessary, in the presence of a catalytic amount or an excess amount of a Lewis acid. Otherwise, the acylation reaction can be conducted in acetone, N,N-dimethylformamide, dimethylsulfoxide, pyridine or a mixture of these solvents, with from 2 to 2.5 equivalent of a carboxylic acid halide or with 2 equivalent or an excess amount of a carboxylic anhydride at a reaction temperature of from 0° to 50° C. for from 0.5 to 10 hours in the presence of from 2 to 3 equivalent or an excess amount of an acid-binding agent.

As the Lewis acid, there may be mentioned, for example, trifluoroacetic acid, methansulfonic acid, p-toluenesulfonic acid, hydrochloric acid, sulfuric acid and boron trifluoride.

As the acid binding agent, there may be mentioned an alkali metal salt such as sodium hydrogen carbonate, potassium hydrogen carbonate, sodium carbonate, potassium carbonate or magnesium oxide, and an organic amine such as triethylamine, ethyldiisopropylamine, N-methylmorpholine, pyridine or N,N-dimethylaniline.

The carboxylic anhydride includes acetic anhydride, propionic anhydride and butyric anhydride.

The carboxylic acid halide includes acetyl chloride, propionyl chloride and butyryl chloride.

The acylation reaction includes N-acylation and O-acylation.

When only N-acylation is conducted, a compound of the formula II wherein the hydroxyl group is protected, is employed as the starting material.

Whereas, when only O-acylation is conducted, a compound of the formula II wherein $R^3$ is a lower alkyl group, an alkanoyl group, an alkylsulfonyl group or an arylsulfonyl group, is employed as the starting material.

When N-acylation and O-acylation are conducted simultaneously, 5,6-dihydroxyindoline obtained by removing the protecting group from the compound of the formula II may be employed. In this case, it is also possible to selectively conducting N-acylation or O-acylation by selecting proper conditions. Selective N-acylation of the compound may be conducted in a protic solvent such as water, methanol, ethanol, propanol, isopropanol, butanol or t-butanol, or in a mixture of water and one of the protic solvents with a carboxylic acid anhydride. Selective O-acylation of the compound may be conducted in a strong acid such as hydrochloric acid, sulfuric acid, phosphoric acid, perchloric acid, trifluoroacetic acid or trifluorosulfonic acid with a carboxylic acid anhydride or a carboxylic acid halide.

Furthermore, by a proper combination of the acylation reaction, the protection of the hydroxyl group or the amino group and the removal of the protecting group for the hydroxyl group or the amino group, it is possible to obtain a compound wherein the O-acyl side chain is different from the N-acyl side chain.

The protection of the hydroxyl group or the amino group can be conducted in accordance with a conventional method.

The protecting reagents commonly employed, include, for instance, methyl iodide, dimethylsulfate, methylene bromide, benzyl bromide, benzyl chloride, acetone, formaldehyde, trioxane, paraformaldehyde, acetaldehyde, methylal, 1,2-dibromoethane, 1,2-dichloroethane, benzyloxycarbonyl chloride, dimethylcarbonate, diethylcarbonate, phosgene and phosgene dimer.

(c) N-alkylation

This N-alkylation reaction is a reaction for producing a 5,6-di-substituted-2-lower alkyl isoindoline by lower-alkylation of the compound of the formula II. The lower alkylation reaction may be conducted by the following method (i), (ii) or (iii).

(i) The compound of the formula II is heated in a solution containing from 1 to 2 equivalent of a lower alkylaldehyde and from 2 to 4 equivalent or an excess amount of formic acid, at a temperature of from 60° to 120° C., whereby the amino group can be converted to a lower alkyl group.

(ii) The compound of the formula II is treated by an addition of from 0.5 to 4 equivalent of sodium borohydride or sodium cyano borohydride in the presence of from 1 to 3 equivalent of a lower alkylaldehyde, whereby the amino group can be converted to a lower alkyl group. As the solvent for the reaction, methanol, ethanol or tetrahydrofuran, or its aqueous solvent may be employed. The reaction can be completed at a temperature of from room temperature to 80° C. However, for smooth reaction, it is preferred to conduct the reaction within a range of from room temperature to 40° C.

(iii) The compound of the formula II is reacted with 1 equivalent of a dialkylsulfate or an alkyl iodide in the presence of a base such as sodium hydrogencarbonate, potassium hydrogencarbonate or calcium carbonate, or in the presence of an almost neutral carbonate such as magnesium carbonate, whereby the amino group can be converted to a lower alkyl group. The reaction can be conducted under cooling with ice or at a temperature of upto 40° C. in water or in an organic solvent such as acetone, acetonitrile, dimethylformamide or dimethylsulfoxide, or a solvent mixture thereof. The lower alkyl aldehyde used for the reaction for N-alkylation includes a aliphatic lower alkyl aldehyde such as formaldehyde, acetaldehyde, propionaldehyde, butyraldehyde, isobutyraldehyde, valeraldehyde, isovaleraldehyde, 2-methylbutyraldehyde, 2-ethylbutyraldehyde, 4-methylpentylaldehyde, 3,3-dimethylbutyraldehyde, 2,2-dimethylpropylaldehyde, cyclopropanecarboxyaldehyde, cyclobutanecarboxyaldehyde or cyclopentanecarboxyaldehyde.

(d) N-aralkylation

This N-aralkylation reaction is a reaction for producing a 5,6-di-substituted-2-aralkylisoindoline by aralkylation of the compound of the formula II.

This aralkylation reaction can be conducted under reaction conditions similar to the above N-alkylation reaction by using an arylaldehyde or aralkylaldehyde instead of the lower alkyl aldehyde used in the N-alkylation. As the arylaldehyde, there may be mentioned, for instance, benzaldehyde, m-methoxybenzaldehyde, p-methoxybenzaldehyde, phenylacetaldehyde, phenylpropionaldehyde, furfural, tetrahydrofurfuraldehyde, 2-thiophenaldehyde, 3-thiophen-aldehyde, nicotinaldehyde, isonicotinaldehyde and picolinaldehyde.

The compound of the formula II can, if necessary, be converted to a compound of the formula I by conducting the subsequent steps (a) to (c). Such steps (a), (b) and (c) may be conducted in any order or repeatedly depending upon the desired compound. Further, if necessary, a step of protecting the hydroxyl group or the amino group or a step of removing the protecting group for the hydroxyl group or the amino group may also be incorporated.

The product in each of the first, second and third steps, may be isolated or may be used without isolation for the next step.

After the completion of the reaction, the compound of the formula I or its salt may be isolated from the reaction solution and purified by conventional means for separation such as solvent extraction, recrystallization and chromatography.

The compounds of the present invention can be converted by conventional methods to inorganic acid salts such as hydrochlorides, hydrobromides, sulfates, nitrates and perchlorates, or to organic sulfonates such as methanesulfonates and p-toluenesulfonates.

The compound of the formula IV used as the starting material for process A, may be prepared from a 3,4-disubstituted benzaldehyde and a corresponding primary amine by reducing the resulting shiff base with hydrogen in the presence of a catalyst such as palladized carbon, or with a hydride reagent such as sodium borohydride or sodium cyanoborohydride.

PROCESS B

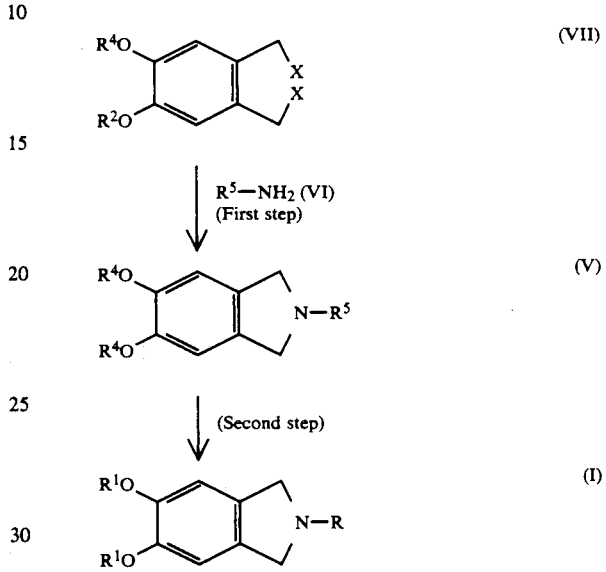

First Step

This step comprises reacting a 4,5-di-substituted-$\alpha,\alpha'$-dihalo-o-xylene derivative of the formula VII with a compound of the formula VI in the presence of an acid binding agent, to form an isoindoline derivative of the formula V.

The reaction is conducted in an organic solvent such as chloroform, methylene chloride, acetone, benzene, toluene, xylene, acetonitrile, dioxane, dimethylformamide or dimethylsulfoxide, or in a two-phase system of such an organic solvent and water, by reacting the compound of the formula VII with from 1 to 1.2 equivalent of the compound of the formula VI in the presence of an acid binding agent. The reaction conditions in the two-phase system are similar to those described with respect to the second step of process A.

As the acid binding agent, from 2 to 6 equivalent or an excessive amount of, for example, an alkali metal hydride such as sodium hydride, an alkali metal hydroxide such as sodium hydroxide or potassium hydroxide, an alkali metal carbonate such as sodium carbonate or potassium carbonate, or an alkali metal hydrogen carbonate such as sodium hydrogen carbonate or potassium hydrogen carbonates. The reaction proceeds smoothly at a temperature of from room temperature to 70° C. for from 5 to 30 hours.

The 4,5-di-substituted-$\alpha,\alpha'$-dihalo-o-xylene derivative of the formula VII used as a starting material in process B, can be prepared by the method disclosed in "Journal of the American Chemical Society"Vol. 72, p.2989 (1952).

As the halogen atom for substitution, chlorine and bromine may be mentioned.

Second Step

This step is an optional step which is conducted to lead the compound of the formula V obtained in the first step to a compound of the formula I, as the case requires.

Namely, the compound of the present invention may be obtained by conducting at least one step selected from the group consisting of (a) acylation, (b) N-alkylation and (c) N-aralkylation. Steps (a) to (c) may be conducted in the same manner as the corresponding steps described with respect to process A.

Now, the present invention will be described in further detail with reference to Examples and reference Examples. However, it should be understood that the present invention is by no means restricted to these specific Examples.

EXAMPLE 1

Preparation of 5,6-dimethoxy-2-methylisoindoline 18.4 g (79.7 mmol) of N-(6-chloromethyl-3,4-dimethoxybenzyl)methylamine hydrochloride was added at 10° C. to a suspension comprising 40 ml of a 50% sodium hydroxide aqueous solution, 200 ml of benzene and 1 ml of a 90% trioctylmethylammonium chloride aqueous solution. The mixture was stirred for 2 hours. Then, the organic layer of the reaction solution was separated, washed with water and a saturated sodium chloride aqueous solution, and dried over anhydrous sodium sulfate. The solvent was distilled off under reduced pressure, and 200 ml of n-hexane was added to the residue. The mixture was boiled for 10 minutes, and subjected to active carbon treatment while the mixture was still hot. The solvent was distilled off under reduced pressure, and the crystalline residue was washed with n-hexane to obtain 9.1 g (yield: 59.0%) of the above identified compound as colorless crystals.

Melting point: 80° C.

IR$\nu$(KBr): 1605, 1500, 1450, 1345, 1330, 1280, 1225, 1190, 1095, 840, 750cm$^{-1}$

NMR$\delta$(CDCl$_3$): 2.56(3H, s), 3.84(10H, s), 6.71(2H, s)

EXAMPLE 2

Preparation of 5,6-dimethoxy-2-methylisoindoline 2 g (50 mmol) of sodium hydroxide was dissolved in 50 ml of water, and 46 ml of benzene was added thereto. While stirring the mixture, 4.6 g (20 mmol) of N-(6-chloromethyl-3,4- dimethoxybenzyl)methylamine hydrochloride was added at a temperature of from 10° to 15° C. The mixture was stirred at room temperature overnight, and then extracted with benzene. The extract was dried over anhydrous sodium sulfate, and the solvent was distilled off under reduced pressure to obtain 3.64 g of a solid residue. Then, 100 ml of n-hexane was added to the solid residue, and the mixture was boiled for 10 minutes, and then subjected to active carbon treatment while the mixture was still hot. The solvent was distilled off under reduced pressure, and the crystalline residue was washed with n-hexane to obtain 3.2 g (yield: 82.9%) of the above identified compound as colorless crystals.

The melting point, the infrared absorption spectrum and the $^1$H-NMR spectrum of this product were the same as those of the compound of Example 1.

EXAMPLE 3

Preparation of 5,6-dimethoxy-2-methylisoindoline 115 mg (0.5 mmol) of N-(6-chloromethyl-3,4-dimethoxybenzyl)methylamine hydrochloride was added to a suspension comprising 175 mg (1.27 mmol) of potassium carbonate and 3 ml of benzene at room temperature under vigorous stirring, and the mixture was vigorously stirred for 15 hours. The reaction solution was filtered, and the solvent was distilled off under reduced pressure to obtain 86 mg (yield: 89.0%) of the above identified compound.

The melting point, the infrared absorption spectrum and the $^1$H-NMR spectrum of this product were the same as those of the compound of Example 1.

EXAMPLE 4

Preparation of 5,6-dimethoxy-2-methylisoindoline hydrochloride 23 g (0.1 mol) of N-(6-chloromethyl-3,4-dimethoxybenzyl)-methylamine hydrochloride was added at a temperature of from 15° to 18° C. to a suspension comprising 50 ml of a 50% sodium hydroxide aqueous solution, 230 ml of benzene and 1 ml of a 90% trioctylmethylammonium chloride aqueous solution over a period of 2 minutes. The mixture was stirred for 3 hours, and then the organic layer of the reaction solution was separated, washed with water and a saturated sodium chloride aqueous solution, and then dried over anhydrous sodium sulfate. The solvent was distilled off under reduced pressure, and 50 ml of 6N hydrochloric acid was added to the residue. The mixture was again evaporated under reduced pressure to dryness. The crystalline residue was washed with ethanol to obtain 12.65 g (yield: 51.2%) of the above identified compound. From the filtrate, 1.8 g (yield: 7.8%) of secondary crystals were obtained. The total amount was 14.4 g (total yield: 63.1%). Melting point: 227° C. (decomposed)

IR$\nu$(KBr): 3425, 2940, 2700–2400, 1620, 1515, 1470, 1335, 1225, 1195, 1100, 1070, 995, 885, 750, 480 cm$^{-1}$

NMR$\delta$(DMSO-d$_6$): 2.94(3H, s), 3.76(6H, s), 4.48(4H, br s), 7.00(2H, s), 12.33(1H, br)

EXAMPLE 5

Preparation of 5,6-dimethoxy-2-p-tolylsulfonylisoindoline 1.89 g (11 mmol) of p-toluenesulfonamide was added to 20 ml of N,N-dimethylformamide, and 3.3 g (24 mmol) of pulverised potassium carbonate and 2.0 g (8.5 mmol) of 4,5-bischloromethyl veratrol were added thereto at room temperature under stirring. The mixture was stirred at room temperature for 20 hours, and after an addition of 40 ml of water, extracted with methylene chloride. The extract was washed with water, and then dried over anhydrous sodium sulfate. The solvent was distilled off under reduced pressure, and the crystalline residue was washed with diisopropyl ether to obtain 2.7 g (yield: 95.2%) of the above identified compound.

Melting point: 167°–168° C.

IR$\nu$(KBr): 1519, 1460, 1340, 1160, 1110, 810, 670, 605, 550, 525cm$^{-1}$

NMR$\delta$(CDCl$_3$): 2.38(3H, s), 3.82(6H, s), 4.56(4H, s), 6.65(2H, s), 7.29(2H, d, J=6.2Hz) 7.49(2H, d, J=6.2Hz)

EXAMPLE 6

Preparation of 2-benzyl-5 6-dimethoxyisoindoline 2.35 g (10 mmol) of 4,5-bischloromethyl veratrol was added at room temperature to a suspension comprising 5 ml of a 50% sodium hydroxide aqueous solution, 25 ml of toluene, 1.25 g (11.66 mmol) of benzylamine and 0.2 g of a Starks catalyst. The mixture was stirred at room temperature for 20 hours, and then the organic layer was separated and dried over anhydrous sodium sulfate. The solvent was distilled off under reduced pressure, and the crystalline residue was washed with isopropyl ether to obtain 1.87 g (yield: 70.0%) of the above identified compound as colorless needle-like crystals.

Melting point: 111° C.
IR$\nu$(KBr): 3100–2700, 1610, 1500, 1465, 1340, 1325, 1280, 1215, 1185, 1100, 990, 845, 835, 760, 695, 485 cm$^{-1}$
NMR$\delta$(CDCl$_3$): 3.73(6H, s), 3.88(6H, s), 6.70(2H, s), 7.20–7.45(5H, m)

EXAMPLE 7

Preparation of 5,6-dimethoxy-2-p-tolylsulfonylisoindoline 100 ml of an N,N-dimethylformamide solution containing 34.2 g (0.20 mol) of p-toluenesulfonamide, was dropwise added over a period of 60 minutes under cooling with ice to a suspension comprising 19.7 g (0.41 mol) of 50% oily sodium hydride and 60 ml of N,N-dimethylformamide. The reaction solution was stirred at room temperature for 30 minutes at 60° C., and then 300 ml of an N,N-dimethylformamide solution containing 47 g (0.20 mol) of 4,5-bischloromethyl veratrol was dropwise added over a period of 90 minutes at 60° C. The reaction solution was stirred at room temperature for 3 hours, and then poured into 2000 ml of water. The precipitated crystals were collected and washed with water to obtain 60 g (yield: 90.0%) of the above identified compound.

The compound was recrystallized from N,N-dimethylformamide. The melting point, the infrared absorption spectrum and the $^1$H-NMR spectrum of this product were the same as those of the compound of Example 5.

EXAMPLE 8

Preparation of 5,6-dihydroxyisoindoline hydrobromide 360 ml of 47% hydrobromic acid, 45 ml of phenol and 60 ml of propionic acid were added to 60 g (0.18 mol) of 5,6-dimethoxy-2-p-tolylsulfonylisoindoline, and the mixture was refluxed for 4 hours under vigorous stirring under a nitrogen atmosphere. The reaction solution was evaporated under reduced pressure to dryness, and 120 ml of 47% hydrobromic acid was added to the residue. The mixture was again refluxed under a nitrogen atmosphere for 3 hours. The reaction solution was cooled, and then 300 ml of water and 300 ml of chloroform were added thereto. The water layer was separated, and subjected to active carbon treatment. The water layer was evaporated under reduced pressure to dryness, and the crystalline residue was washed with ether/ethanol (1/1) to obtain 25.62 g (yield: 61.4%) of the above identified compound.

Melting point: 251° C. (decomposed)
IR$\nu$(KBr): 1610, 1510, 1460, 1450, 1410, 1330, 1290cm$^{-1}$
NMR$\delta$(DMSO-d$_6$): 4.40(4H, br s), 6.85(2H, s), 8.80(2H, br), 9.55(2H, br)

EXAMPLE 9

Preparation of 2-benzyl-5,6-dihydroxyisoindoline hydrobromide 3.54 ml of 48% hydrobromic acid was added to 500 mg (1.86 mmol) of 2-benzyl-5,6-dimethoxyisoindoline, and the mixture was refluxed for 3 hours under stirring. The precipitated crystals were collected from the reaction solution, and washed with water and acetone to obtain 578 mg (yield: 96.5%) of the above identified compound as colorless prism crystals.

Melting point: 148° C.
IR$\nu$(KBr): 3650–2200, 1600, 1510, 1460, 1400, 1330, 1285, 1150, 1095, 700, 490cm$^{-1}$
NMR$\delta$(DMSO-d$_6$): 3.00–4.00(2H, m), 4.43(4H, br s), 4.60(2H, br s), 6.78(2H, s) 7.30–7.80(5H, m)

EXAMPLE 10

Preparation of 5,6-dihydroxyisoindoline hydrobromide 200 mg (0.621 mmol) of 2-benzyl-5,6-dihydroxyisoindoline hydrobromide was dissolved in 3 ml of methanol, and 14 mg of 10% palladium carbon was added thereto. Under a hydrogen gas stream, catalytic reduction was conducted at 50° C. for 9 hours. The solvent was distilled off under reduced pressure, and the crystalline residue was washed with acetone to obtain 136 mg (yield: 94.4%) of the above identified compound as colorless prism crystals.

The melting point, the infrared absorption spectrum and the $^1$H-NHR spectrum of this product were the same as those of the compound of Example 8.

EXAMPLE 11

Preparation of 5,6-dimethoxyisoindoline 1.20 g (4.46 mmol) of 2-benzyl-5,6-dimethoxyisoindoline was dissolved in 40 ml of methanol at 40° C., and 84 mg of 10% palladium carbon was added thereto. Under a hydrogen stream, catalytic reduction was conducted at the same temperature for 4 hours. The solvent was distilled off under reduced pressure, and a small amount of ethyl acetate and diethylether was added to the residue and stirred. The precipitates were collected to obtain 617 mg (yield: 77.3%) of the above identified compound.

Melting point: 131° C. (decomposed)
IR$\nu$(KBr): 3360, 3100–2500, 1610, 1500, 1460, 1270, 1210, 1090, 850, 740, 680cm$^{-1}$
NMR$\delta$(CDCl$_3$): 2.54(1H, s), 3.87(6H, s), 4.18 (4H, s), 6.77(2H, s)

EXAMPLE 12

Preparation of 5,6-dimethoxyisoindoline hydrochloride 1.00 g (3.72 mmol) of 2-benzyl-5,6-dimethoxyisoindoline was dissolved in 50 ml of methanol at 40° C., and then 1.24 g (7.44 mmol) of 6N hydrochloric acid and 70 mg of 10% palladium carbon were added thereto. Under a hydrogen gas stream, catalytic reduction was conducted at the same temperature. The solvent was distilled off under reduced pressure, and the crystalline residue was washed with acetone to obtain 758 mg (yield: 94.3%) of the above identified compound as colorless prism crystals.

Melting point: 220–230 ° C. (decomposed)
IR$\nu$(KBr): 3410, 3200–2300, 1610, 1510, 1280, 1220, 1095, 1010, 840, 470cm$^{-1}$
NMR$\delta$(DMSO-d$_6$) 3.78(6H, s), 4.40(4H, s), 7.00(2H, s) 10.20–10.60(2H, m)

EXAMPLE 13

Preparation of 5,6-dihydroxyisoindoline hydrobromide 3.54 ml of 48% hydrobromic acid was added to 500 mg (2.79 mmol) of 5,6-dimethoxyisoindoline, and the mixture was refluxed for 3 hours under stirring. The precipitated crystals were collected, and washed with ethanol/diethyl ether (1/1) to obtain 520 mg (80.3%) of the above identified compound.

The melting point, the infrared absorption spectrum and the $^1$H-NHR spectrum of this product were the same as those of the compound of Example 8.

EXAMPLE 14

Preparation of 5,6-dihydroxy-2-methylisoindoline hydrobromide 15.39 g (66 mmol) of 5,6-dihydroxyisoindoline hydrobromide and 4.48 g (66 mmol) of sodium formate were dissolved in 100 ml of a 50% formic acid aqueous solution, and then 5.17 ml (70 mmol) of 37% formalin was added thereto. The mixture was heated at 80° C. for 4 hours. Then, the reaction solvent was distilled off under reduced pressure, and 200 ml of 23% hydrobromic acid was added to the residue. The mixture was subjected to active carbon treatment. The filtrate was again evaporated under reduced pressure to dryness, and the crystalline residue was recrystallized from water to obtain 11.74 g (yield: 72.3%) of the above identified compound.

Melting point : 205° C. (decomposed)
IR$\nu$(KBr): 1605, 1505, 1460, 1445, 1320, 1280, 1175, 855, 635cm$^{-1}$
NMR$\delta$(DMSO-d$_6$): 2.99(3H, s), 4.10–4.80(4H, br d), 6.78(2H, s), 9.00(1H, br), 10.83(1H, br s)

EXAMPLE 15

Preparation of 5,6-dimethoxy-2-methylisoindoline 157 mg (2.31 mmol) of sodium formate, 0.85 ml of a 50% formic acid aqueous solution and 0.21 ml (2.85 mmol) of 37% formalin were added to 500 mg (2.31 mmol) of 5,6-dimethoxyisoindoline hydrochloride. The mixture was stirred at 80° C. for 3 hours. Then, the solvent was distilled off under reduced pressure and a water was added to the residue. The mixture was made alkaline with a 2N sodium hydroxide aqueous solution, and then extracted with methylene chloride. The extract was dried over anhydrous sodium sulfate and subjected to active carbon treatment. The solvent was distilled off under reduced pressure to obtain 427 mg (yield: 95.8%) of the above identified compound as colorless needle-like crystals.

The melting point, the infrared absorption spectrum and the $^1$H-NMR spectrum of this product were the same as those of the compound of Example 1.

EXAMPLE 16

Preparation of 5,6-dihydroxy-2-methylisoindoline 15.39 g (66 mmol) of 5,6-dihydroxyisoindoline hydrobromide and 4.48 g (66 mmol) of sodium formate were dissolved in 100 ml of a 50% formic acid aqueous solution, and then 5.17 ml (70 mmol) of 37% formalin was added thereto. The mixture was stirred at 80° C. for 4 hours. Then, the solvent was distilled off under reduced pressure, and the residue was dissolved in 200 ml of water and subjected to active carbon treatment. The active carbon was filtered off, and the filtrate was stirred under cooling with ice, and adjusted to pH 8.0 with a saturated sodium hydrogen carbonate aqueous solution, and then it was stirred at the same temperature for about 30 minutes. The precipitates were collected, and washed with water to obtain yellowish green primary crystalline powder. This powder was combined with secondary crystalline powder obtained from the filtrate, and after an addition of 300 ml of water, stirred for 30 minutes. The insolubles was collected to obtain 7.87 g (yield: 72.3%) of the above identified compound.

Melting point: 170–180° C. (decomposed)
IR$\nu$(KBr): 1600, 1515, 1355, 1320, 1220cm$^{-1}$
NMR$\delta$(DMSO-d$_6$): 2.42(3H, s), 3.64(4H, br s), 6.56(2H, s)

EXAMPLE 17

Preparation of 5,6-dihydroxy-2-methylisoindoline hydrobromide 15.39 g (66 mmol) of 5,6-dihydroxyisoindoline hydrobromide and 4.48 g (66 mmol) of sodium formate were dissolved in 100 ml of a 50% formic acid aqueous solution, and 5.17 ml (70 mmol) of 37% formalin was added thereto. The mixture was stirred at 80° C. for 4 hours. Then, the solvent was distilled off under reduced pressure, and the residue was dissolved in 50 ml of water by warming. Then, the solvent was again distilled off under reduced pressure. The residue was dissolved in 100 ml of methanol by warming, and the solution was concentrated under reduced pressure to about 20 ml. The insolubles were collected, dissolved in 23 ml of water and subjected to active carbon treatment. The active carbon was filtered off, and 5 ml of 48% hydrobromic acid was added to the filtrate. The mixture was left to stand overnight under cooling with ice. The precipitated crystals were collected to obtain 6.3 g (yield: 58.0%) of the above identified compound as colorless prism crystals.

The melting point, the infrared absorption spectrum and the $^1$H-NMR spectrum of this product were the same as those of the compound of Example 14.

EXAMPLE 18

Preparation of 5,6-dihydroxy-2-methylisoindoline hydrobromide 15.39 g (66 mmol) of 5,6-dihydroxyisoindoline hydrobromide and 4.48 g (66 mmol) of sodium formate were dissolved in 100 ml of a 50% formic acid aqueous solution, and 5.17 ml (70 mmol) of 37% formalin was added thereto. The mixture was stirred at 80° C. for 4 hours. The solvent was distilled off under reduced pressure, and the residue was dissolved in 50 ml of water under warming. The solvent was again distilled off under reduced pressure. The residue was dissolved in 40 ml of water and subjected to active carbon treatment. The active carbon was filtered off, and 2.5 ml of concentrated aqueous ammonia was added to the filtrate under a nitrogen stream at room temperature. The mixture was left to stand for 2 hours under cooling with ice. The precipitates were collected, and dissolved in 24 ml of water and 3.0 ml of 48% hydrobromic acid. The solution was subjected to active carbon treatment. The active carbon was filtered off, and the filtrate was concentrated under reduced pressure to about 10 ml. Then, 10 ml of 48% hydrobromic acid was added thereto, and the mixture was left to stand overnight under cooling with ice. The precipitated crystals were collected to obtain 4.0 g (yield: 65.0%) of the above identified compound as colorless prism crystals.

The melting point, the infrared absorption spectrum and the $^1$H-NMR spectrum of this product were the same as those of the compound of Example 14.

EXAMPLE 19

Preparation of 5,6-dihydroxy-2-methylisoindoline hydrobromide 130 ml of 48% hydrobromic acid was added to 13.2 g (68.3 mmol) of 5,6-dimethoxy-2-methylisoindoline, and the mixture was refluxed for 7 hours under boiling. The reaction solution was evaporated under reduced pressure to dryness, and 100 ml of water was added to the residue. The mixture was subjected to active carbon treatment. The filtrate was concentrated under reduced pressure to about 30 ml, and cooled with ice. The precipitated crystals were collected and washed first with methanol and then with acetone to obtain 11.9 g (yield: 70.8%) of the above identified compound as colorless crystals.

The melting point, the infrared absorption spectrum and the $^1$H-NMR spectrum of this product were the same as those of the compound of Example 14.

EXAMPLE 20

Preparation of 5,6-diacetoxy-2-methylisoindoline hydrobromide 500 mg (12.03 mmol) of 5,6-dihydroxy-2-methylisoindoline hydrobromide was dissolved in 2.5 ml of pyridine, and 2.5 ml of acetic anhydride was added thereto at room temperature. The mixture was stirred at 40° C. for 30 minutes, and excess pyridine and acetic anhydride were distilled off under reduced pressure, and the crystalline residue was washed with methylene chloride/ether (1/1) to obtain 616 mg (yield: 91.9%) of the above identified compound.

Melting point: 220° C.

IR$\nu$(KBr): 3420, 2930, 2800–2300, 1760, 1490, 1365, 1210, 1170, 1070, 1010, 910cm$^{-1}$

NMR$\delta$(DMSO-d$_6$): 2.32(6H, s), 3.06(3H, s), 4.66(4H, br s), 7.36(2H, br s)

EXAMPLE 21

Preparation of 5,6-diacetoxy-2-acetylindoline 500 mg (2.15 mmol) of 5,6-dihydroxyisoindoline hydrobromide was dissolved in 2.5 ml of pyridine, and 2.5 ml of acetic anhydride was added thereto at room temperature. The mixture was stirred at the same temperature for 30 minutes, and then excess pyridine and acetic anhydride were distilled off under reduced pressure. Ethyl acetate was added to the residue, and insoluble matters were filtered off. The filtrate was concentrated under reduced pressure, and the crystalline residue was washed with ethyl ether to obtain 532 mg (yield: 89.0%) of the above identified compound.

Melting point: 127° C.

IR$\nu$(KBr): 3430, 2860, 1775, 1765, 1645cm$^{-1}$

NMR$\delta$(DMSO-d$_6$): 202(3, s), 2.26(6H, s), 4.58(2H, br s), 4.79(2H, br s), 7.22(2H, br s)

EXAMPLE 22

Preparation of 5,6-dihydroxy-2-methylisoindoline hydrobromide 300 mg (1.29 mmol) of 5,6-dihydroxyisoindoline hydrobromide was dissolved in 4 ml of a 50% methanol aqueous solution, and 0.24 ml (3.2 mmol) of 37% formalin was added thereto. The mixture was stirred at room temperature for an hour. Then 1 ml of 48% hydrobromic acid was gradually added to the mixture, and the solvent was distilled off under reduced pressure. The residue was dissolved in 5 ml of water, and the solvent was concentrated under reduced pressure. The precipitated crystals were collected and washed first with methanol and then with acetone to obtain 216 mg (yield: 68.1%) of the above identified compound.

The melting point, the infrared absorption spectrum and the $^1$H-NMR spectrum of this product were the same as those of the compound of Example 14.

EXAMPLE 23

Preparation of 5,6-dimethoxy-2-methylisoindoline 600 mg (2.78 mmol) of 5,6-dimethoxyisoindoline hydrochloride was dissolved in 8 ml of a 50% methanol aqueous solution, and 0.24 ml (3.2 mmol) of 37% formalin was added thereto. Under cooling with ice, 129 mg (3.4 mmol) of sodium borohydride was gradually added to the mixture, and then the mixture was stirred at room temperature for an hour. The mixture was made alkaline with a 2N sodium hydroxide aqueous solution, and then extracted with methylene chloride. The extract was dried over anhydrous sodium sulfate. The solvate was distilled off under reduced pressure to obtain 537 mg (yield: 100%) of the above identified compound as colorless needle-like crystals.

The melting point, the infrared absorption spectrum and $^1$H-NMR spectrum of this product were the same as those of the compound of Example 1

REFERENCE EXAMPLE 1

Preparation of N-(3,4-dimethoxybenzyl)methylamine 41.5 g (0.25 mol) of veratraldehyde was suspended in 100 ml of water, and 29 ml of a 40% methylamine aqueous solution was dropwise added over a period of 15 minutes under cooling with ice. The mixture was stirred overnight at room temperature.

500 ml of toluene was added to the reaction solution. The organic layer was separated, and dried over anhydrous sodium sulfate. The solvent was distilled off under reduced pressure to obtain 49.8 g of oily residue of N-(3,4-dimethoxybenzylidene)methylamine.

This oily residue was dissolved in 300 ml of ethanol, and 10 g of 10% palladium carbon was added. Under a hydrogen gas stream, catalytic reduction was conducted for 7 hours. The catalyst was removed from the reaction solution, and the solvent was distilled off under reduced pressure to obtain 45 g (yield: 100%) of the above identified compound as oily residue.

NMR$\delta$(CDCl$_3$): 1.67(1H, s), 2.45(3H, s), 3.68(2H, s), 3.89(6H, s), 6.80–6.95(3H, m)

REFERENCE EXAMPLE 2

Preparation N-(6-chloromethyl-3,4-dimethoxybenzyl)-methylamine hydrochloride 150 ml of concentrated hydrochloric acid was added to a suspension comprising 13.5 g (74.5 mmol) of N-(3,4-dimethoxybenzyl)methylamine and 6.75 g (225 mmol) of paraformaldehyde under stirring under cooling with ice, and the mixture was stirred at 50° C. for 5 hours. The mixture was evaporated under reduced pressure at 50° C. to dryness, and 50 ml of acetone was added to the crystalline residue. One hour later, crystals were collected and washed with acetone to obtain 12.39 g (yield: 72.1%) of primary crystals. The filtrate and washing solutions were put together, and the solvent was distilled off under reduced pressure to obtain 670 mg (yield: 3.9%) of secondary crystals. The total amount was 13.06 g (total yield: 76.0%).

Melting point: 174° C.

IRν(KBr): 1600, 1525, 1460, 1275, 1230, 1100, 1000, 875cm$^{-1}$

NMRδ(DMSO-d$_6$): 2.25(3H, s), 3.76(3H, s), 3.81(3H, s), 4.12(2H, br s), 4.93(2H, s), 7.09(1H, s), 7.43(1H, s)

The compounds of the present invention are novel compounds not disclosed in literatures, and they can be readily prepared in good yield by using 4,5-di-substituted-α,α'-dihalo-o-xylene derivatives or N-(3,4-di-substituted benzyl)lower alkyl amines as starting materials.

The compounds of the present invention are useful as intermediates for cephalosporin derivatives (antibacterial agents) having a 5,6-dialkanoyl-2-methylisoindoliniomethyl group such as 5,6-dihydroxy-2-methylisoindoliniomethyl or 5,6-diacetoxy-2-methylisoindoliniomethyl, at the 3-position of the cephem nucleus.

What is claimed is:

1. A compound having the formula:

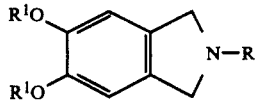

wherein R is a hydrogen atom a C$_{1-4}$ alkyl group, an alkanoyl group having from 2 to 5 carbon atoms, an aralkyl group having from 7 to 12 carbon atoms, a methanesulfonyl group, an ethanesulfonyl group, a benzenesulfonyl group or a p-toluenesulfonyl group, and R$^1$ is a hydrogen atom or a hydroxyl-protecting group selected from the group consisting of acetyl, methyl, benzyl and ethoxycarbonyl, or two R$^1$ groups of adjacent OR$^1$ groups together form methylene, ethylene or isopropylidene, or a salt thereof.

* * * * *